US012661092B2

(12) United States Patent
Schoeman et al.

(10) Patent No.: US 12,661,092 B2
(45) Date of Patent: Jun. 23, 2026

(54) INGESTIBLE DEVICE FOR SAMPLING MATERIAL AND METHOD FOR USING THE SAME

(71) Applicant: Stichting IMEC Nederland, Wageningen (NL)

(72) Inventors: Rogier Schoeman, Wageningen (NL); Klaus Mathwig, Eindhoven (NL)

(73) Assignee: Stichting IMEC Nederland, Wageningen (NL)

( * ) Notice: Subject to any disclaimer, the term of this patent is extended or adjusted under 35 U.S.C. 154(b) by 392 days.

(21) Appl. No.: 18/320,766

(22) Filed: May 19, 2023

(65) Prior Publication Data

US 2023/0380816 A1      Nov. 30, 2023

(30) Foreign Application Priority Data

May 25, 2022     (EP) ..................................... 22175289

(51) Int. Cl.
*A61B 10/00*           (2006.01)

(52) U.S. Cl.
CPC .. *A61B 10/0045* (2013.01); *A61B 2010/0061* (2013.01); *A61B 2562/162* (2013.01)

(58) Field of Classification Search
CPC ........ A61B 10/0045; A61B 2010/0061; A61B 2562/162
See application file for complete search history.

(56) References Cited

U.S. PATENT DOCUMENTS

| | | | | |
|---|---|---|---|---|
| 5,024,663 A | * | 6/1991 | Yum | ................ A61B 5/150221 |
| | | | | 604/141 |
| 2009/0012503 A1 | | 1/2009 | Kawano et al. | |

| | | | | |
|---|---|---|---|---|
| 2015/0011874 A1 | * | 1/2015 | Amoako-Tuffour | ........................ |
| | | | | A61M 31/002 |
| | | | | 604/503 |
| 2019/0223846 A1 | * | 7/2019 | Kerkhof | ............. A61B 10/0045 |
| 2019/0274663 A1 | | 9/2019 | Rees et al. | |
| 2020/0237349 A1 | | 7/2020 | Duan et al. | |
| 2021/0213263 A1 | | 7/2021 | Rhodes et al. | |
| 2021/0228157 A1 | | 7/2021 | Jones | |
| 2021/0345904 A1 | | 11/2021 | Moshiree et al. | |

(Continued)

FOREIGN PATENT DOCUMENTS

| | | |
|---|---|---|
| CN | 1820798 A | 8/2006 |
| CN | 113081075 A | 7/2021 |

(Continued)

OTHER PUBLICATIONS

Extended European Search Report and Search Opinion, Application No. EP 22175289.2, mailed Nov. 22, 2022, 10 pages.

*Primary Examiner* — Daniel L Cerioni

(74) *Attorney, Agent, or Firm* — McDonnell Boehnen Hulbert & Berghoff LLP

(57)                    ABSTRACT

An ingestible device for sampling material at least one time is provided. The ingestible device includes a first chamber that is enlargeable in volume and that includes an inlet, and that can be filled with the material to be sampled, a second chamber that is diminishable in volume and that includes an outlet, and a reversible actuating mechanism. The reversible actuating mechanism is configured such that triggering the reversible actuating mechanism leads to an enlargement of the first chamber to collect the material to be sampled through the inlet and also leads to a diminishment of the second chamber.

19 Claims, 5 Drawing Sheets

(56) References Cited

U.S. PATENT DOCUMENTS

| | | | | |
|---|---|---|---|---|
| 2022/0175351 A1* | 6/2022 | Shalon | ................. | C12Q 1/6886 |
| 2023/0035768 A1* | 2/2023 | Nejati | .................... | A61B 10/02 |
| 2024/0237973 A1* | 7/2024 | Steinsland | ......... | A61B 10/0045 |

FOREIGN PATENT DOCUMENTS

| | | | |
|---|---|---|---|
| WO | 2018133660 A1 | 7/2018 |
| WO | 2020193267 A1 | 10/2020 |

* cited by examiner

INGESTIBLE DEVICE FOR SAMPLING MATERIAL AND METHOD FOR USING THE SAME

CROSS-REFERENCE TO RELATED APPLICATIONS

The present application is a non-provisional patent application claiming priority to European Patent Application No. EP 22175289.2, filed on May 25, 2022, the contents of which are hereby incorporated by reference.

FIELD OF THE DISCLOSURE

The present disclosure relates to an ingestible device for sampling material at least one time and a method for using such an ingestible device.

BACKGROUND

Endoscopy is often performed to gather information and or samples from the gastrointestinal (GI) tract. Endoscopes often comprise long tubes that can be equipped with a camera, cutting tools, and hollow needles. The proximal and distal parts of the GI tract are reachable via endoscopy. Unfortunately, the endoscopic procedure is rather unpleasant for the patient. Additionally, the small intestine cannot be reached via this procedure. Thus, a device that enables investigation of the small intestine contents could be beneficial. Additionally, actively controlled local drug delivery in the GI tract is challenging.

US 2021/0345904 A1 relates to an ingestible capsule device that collects fluid aspirates from locations within the body, locations such as the small intestine, and retains the fluid aspirates free from contamination as the capsule device is expelled from the body. The capsule device employs a peristaltic pump fluid control within the capsule device, and a single semi-permeable bladder stores collected fluid aspirate. Disadvantageously, due to the usage of the peristaltic pump and the high energy demand and space requirement associated therewith, this ingestible capsule device cannot provide enough energy and free space for sensors to measure the GI fluid in real time.

SUMMARY

An ingestible device and a method for using such an ingestible device are provided herein, such embodiments providing enough energy and free space for sensors to measure, e.g., GI fluid in real time. These benefits are facilitated in part by the use of an energy-saving and space-saving actuating mechanism.

According to a first aspect of the present disclosure, an ingestible device for sampling material at least one time is provided. The ingestible device comprises a first chamber that is enlargeable in volume, comprising an inlet, and to be filled with the material to be sampled, a second chamber being diminishable in space, comprising an outlet, and a reversible actuating mechanism. In this context, the reversible actuating mechanism is configured such that triggering the reversible actuating mechanism leads to an enlargement of the first chamber to collect the material to be sampled through the inlet and to a diminishment of the second chamber. The enlargement and the diminishment may occur simultaneously. This allows for an energy-saving, and thus also space-saving, actuating mechanism, thereby enabling the provision of enough energy and free space for sensors exemplarily measuring GI fluid in real time.

With respect to the reversible actuating mechanism, it is noted that the reversible actuating mechanism can manually be brought into its inactivated state after it has been activated or after the usage of the ingestible device, respectively. In this context, the reversible actuating mechanism may typically be brought into its inactivated state not in situ.

In addition to this, it is noted that triggering the reversible actuating mechanism may comprise actively triggering the reversible actuating mechanism exemplarily in a remote manner.

As a further benefit, it is noted that the ingestible device can be used for applications including human patients as well as animal health.

According to a first implementation form of a first aspect of the present disclosure, the first chamber collects the material through the inlet due to an under pressure, wherein the inlet is sealed when the material is collected. Additionally or alternatively, the second chamber contains a substance to be released through the outlet due to an over pressure when the second chamber is diminished. Further additionally or further alternatively, the ingestible device further comprises a third chamber being enlargeable in space, comprising a further inlet, and to be filled with further material to be sampled, a fourth chamber being diminishable in space, comprising a further outlet, and containing a further substance to be released, and a further reversible actuating mechanism. In this context, the further reversible actuating mechanism is configured such that triggering the further reversible actuating mechanism leads to an enlargement of the third chamber, the third chamber thereby taking in further material through the further inlet due to an under pressure, and to a simultaneous diminishment of the fourth chamber, the fourth chamber thereby releasing the further substance through the further outlet due to an over pressure. For instance, a second sample can be taken with the same ingestible device at a different location in the GI tract.

Such an ingestible device can be used for simultaneously sampling the material and releasing the substance at least one time.

The inlet and the outlet may be arranged such that the corresponding physical distance is large enough to exclude taking in material into the inlet that is released from the outlet.

It is noted that the substance can exemplarily be a gas, e.g., an inert gas, or a liquid, e.g., an inert liquid, for example in applications where sampling is desired without a medical treatment of the GI tract.

It is further noted that the further substance can exemplarily be a gas, e.g., an inert gas, or a liquid, e.g., an inert liquid, for example in applications where sampling is desired without a medical treatment of the GI tract.

With respect to the further reversible actuating mechanism, it is noted that the further reversible actuating mechanism can manually be brought into its inactivated state after it has been activated or after the usage of the ingestible device, respectively.

The further inlet and the further outlet can be arranged such that the corresponding physical distance is large enough to exclude taking in material into the further inlet that is released from the further outlet.

According to a second implementation form of the first aspect of the present disclosure, the first chamber and the second chamber are axisymmetric and/or point-symmetric with respect to the third chamber and the fourth chamber. Additionally or alternatively, the first chamber and the second chamber and/or the third chamber and the fourth chamber are rotationally symmetric with respect to the same axis. In addition to this or as an alternative, the reversible actuating mechanism is axisymmetric and/or point-symmetric with respect to the further reversible actuating mechanism, for example if the further reversible actuating mechanism is rotated through degrees. Further additionally or further alternatively, the reversible actuating mechanism and the further reversible actuating mechanism, for example if the further reversible actuating mechanism rotated through 90 degrees, are rotationally symmetric with respect to the same axis.

The first chamber may be point-symmetric with the third chamber and/or the second chamber may be point-symmetric with the fourth chamber, wherein the respective point may be the center of the ingestible device.

Additionally or alternatively, the first chamber may be mirror-symmetric with the third chamber and/or the second chamber may be mirror-symmetric with the fourth chamber, wherein the respective mirror plane may be a cross section in the center of the ingestible device.

With respect to the above-mentioned 90 degrees rotation, it is noted that the rotation may be a 90 degrees rotation around the respective long axis. Additionally or alternatively, the two major segments or halves, respectively, of the ingestible device may be substantially identical, and may be arranged such that they are rotated 180 degrees around a short axis and 90 degrees around the long axis with respect to each other.

According to a further implementation form of the first aspect of the present disclosure, the reversible actuating mechanism comprises: a spring being compressed if the reversible actuating mechanism has not been triggered yet, an electrically conductive alloy portion being conductively connected to an energy source if the reversible actuating mechanism is triggered. In this context, the electrically conductive alloy portion is configured such that connecting the electrically conductive alloy portion to the energy source leads to a reversible deformation of the electrically conductive alloy portion due to Joule heating. Additionally, the spring is arranged with respect to the electrically conductive alloy portion such that the reversible deformation of the electrically conductive alloy portion leads to a decompression of the spring. Further additionally, the spring is arranged with respect to the first chamber such that the first chamber is enlarged in the case of the decompression of the spring. In further addition to this, the spring is arranged with respect to the second chamber such that the second chamber is diminished in the case of the decompression of the spring. For instance, due to Joule heating, both energy and space can be saved in a particularly efficient manner.

The first chamber and the second chamber may be configured similar to a suspension fork principle, i.e., dampening of the spring extension by slow release of liquid from the second chamber through a small outlet orifice. Accordingly, slow sampling within minutes will reduce the chance of only catching a gas bubble.

The electrically conductive alloy of the electrically conductive alloy portion may be a shape-memory alloy, e.g., an electrically conductive shape-memory alloy.

According to a further implementation form of the first aspect of the present disclosure, the reversible actuating mechanism further comprises at least one ball release member. In this context, the at least one ball release member is configured such that the reversible deformation of the electrically conductive alloy portion leads to a movement of the at least one ball release member into at least one indentation, thereby decompressing the spring. For example, the reversible actuating mechanism can be implemented in a very space-saving manner.

With respect to the above-mentioned decompressing the spring, it is noted that the decompressing can also decompress the spring because the at least one ball release member does not necessarily act on the spring in a direct manner to decompress it. In this context, the at least one ball release member may move out of the respective way such that the spring can extend.

According to a further implementation form of the first aspect of the present disclosure, the further reversible actuating mechanism further comprises at least one further ball release member. In this context, the at least one further ball release member is configured such that the further reversible deformation of the further electrically conductive alloy portion leads to a movement of the at least one further ball release member into at least one further indentation, thereby decompressing the further spring. For instance, in this manner, space requirements can be reduced thereby providing free space for sensors or the like.

With respect to the above-mentioned decompressing the further spring, it is noted that the decompressing can also be enabling decompressing the further spring because the at least one further ball release member does not necessarily act on the further spring in a direct manner to decompress it. In this context, the at least one further ball release member may move out of the respective way such that the further spring can extend.

According to a further implementation form of the first aspect of the present disclosure, the further reversible actuating mechanism comprises a further spring being compressed if the further reversible actuating mechanism has not been triggered yet, a further electrically conductive alloy portion being conductively connected to a further energy source if the further reversible actuating mechanism is triggered. In this context, the further electrically conductive alloy portion is configured such that connecting the further electrically conductive alloy portion to the further energy source leads to a reversible deformation of the further electrically conductive alloy portion due to Joule heating. Additionally, the further spring is arranged with respect to the further electrically conductive alloy portion such that the reversible deformation of the further electrically conductive alloy portion leads to a decompression of the further spring. Further additionally, the further spring is arranged with respect to the third chamber such that the third chamber is enlarged in the case of the decompression of the further spring. In further addition to this, the further spring is arranged with respect to the fourth chamber such that the fourth chamber is diminished in the case of the decompression of the further spring. The electrically conductive alloy of the further electrically conductive alloy portion may be a further shape-memory alloy, e.g., a further electrically conductive shape-memory alloy.

The third chamber and the fourth chamber may be configured similar to a suspension fork principle, i.e., dampening of the further spring extension by slow release of liquid from the fourth chamber through a small outlet orifice. Accordingly, slow sampling within minutes will reduce the chance of only catching a gas bubble.

According to a further implementation form of the first aspect of the present disclosure, the inlet comprises a valve, for example a passive valve, which may be a passive one-way valve, e.g., an umbrella valve. Additionally or alternatively, in the case of the presence of the further inlet, the further inlet comprises a further valve, for example a further passive valve, which may be a further passive one-way valve, e.g., a further umbrella valve. The umbrella valve and/or the further umbrella valve may be made of silicon rubber.

The outlet can include an outlet valve, for example a passive outlet valve, which may be a passive one-way outlet valve, e.g., an umbrella outlet valve. Additionally or alternatively, in embodiments that include a further outlet, the further outlet may comprise a further outlet valve, for example a further passive outlet valve, which may be a further passive one-way outlet valve, e.g., a further umbrella outlet valve. The umbrella outlet valve and/or the further umbrella outlet valve may be made of silicon rubber. The umbrella outlet valve and the umbrella valve may be of the same type. Analogously, the further umbrella outlet valve and the further umbrella valve may be of the same type.

The umbrella outlet valve and/or the further umbrella outlet valve is configured to prevent release any substance before triggering.

According to a further implementation form of the first aspect of the present disclosure, the first chamber comprises a removable portion, e.g., a screwable cap, for access to the internal space of the first chamber. Additionally or alternatively, in the case of the presence of the third chamber, the third chamber comprises a further removable portion, e.g., a further screwable cap, for access to the internal space of the third chamber. This allows for simplified sample retrieval.

According to a further implementation form of the first aspect of the present disclosure, the material comprises or is gastrointestinal content. Additionally or alternatively, the substance comprises or is a drug. Further additionally or further alternatively, in the case of the presence of the further material, the further material comprises or is further gastrointestinal content. In further addition to this or as a further alternative, in the case of the presence of the further substance, the further substance comprises or is a further drug. For example, a simultaneous medical treatment of the GI tract is enabled in a particularly efficient manner.

According to a further implementation form of the first aspect of the present disclosure, at least a part of the inner space of the first chamber comprises a stabilizing substance, e.g., a quencher, which may be provided to prevent the material from additional chemical reactions. Additionally or alternatively, in the case of the presence of the third chamber, at least a part of the inner space of the third chamber comprises a further stabilizing substance, e.g., a further quencher, for preventing the further material from additional chemical reactions. For instance, digestion and fermentation of the sampled content can be prevented in a particularly efficient manner.

According to a further implementation form of the first aspect of the present disclosure, the ingestible device further comprises a body portion providing a hollow inner space which may be sealed against the environment of the body portion exemplarily with the aid of at least one sealing, e.g., in the form of an O-ring. In this context, the first chamber and the second chamber are attached to the body portion. Additionally or alternatively, in the case of the presence of the third chamber and the fourth chamber, the third chamber and the fourth chamber are attached to the body portion, e.g., in a symmetric manner to the first chamber and the second chamber. In such examples, sample contamination can be prevented in a cost-efficient manner.

According to a further implementation form of the first aspect of the present disclosure, the body portion, e.g., the hollow inner space of the body portion, comprises at least one of an energy source for supplying the reversible actuating mechanism and/or in the case of the presence of the further reversible actuating mechanism, for supplying the further reversible actuating mechanism, a remote trigger unit, being supplied by the energy source, for receiving at least one remote trigger signal in order to trigger the reversible actuating mechanism and/or in the case of the presence of the further reversible actuating mechanism, to trigger the further reversible actuating mechanism, a data recording unit for recording data, e.g., environment data and/or localization data, during usage of the ingestible device, a wireless data transmission unit for wirelessly transmitting data, for example environment data and/or localization data, e.g., environment data and/or localization data in real time, during usage of the ingestible device. Additionally or alternatively, the body portion, e.g., a portion other than the hollow inner space of the body portion, comprises at least one sensor, e.g., a pH-value sensor. For instance, there is plenty of room for the energy source, electronics such as communication, e.g., wireless communication, and at least one antenna, and sensors.

According to a further implementation form of the first aspect of the present disclosure, the ingestible device has the shape of a pill or a cylinder. Additionally or alternatively, the length of the ingestible device is lower than 24 millimeters, for example lower than 23 millimeters, e.g., after the reversible actuating mechanism has been triggered and/or in the case of the presence of the further reversible actuating mechanism, the further reversible actuating mechanism has been triggered. Further additionally or further alternatively, the diameter of the ingestible device is lower than 9 millimeters, for example lower than 8 millimeters, e.g., after the reversible actuating mechanism has been triggered and/or in the case of the presence of the further reversible actuating mechanism, the further reversible actuating mechanism has been triggered. For example, the ingestible device can be small enough in size that it can easily be swallowed.

According to a second aspect of the present disclosure, a method for using an ingestible device according to any of the implementation forms of the first aspect is provided. The method comprises the step of triggering the reversible actuating mechanism by a first remote trigger signal and/or in the case of the presence of the further reversible actuating mechanism, triggering the further reversible actuating mechanism by transmitting a second remote trigger signal.

BRIEF DESCRIPTION OF THE FIGURES

The above, as well as additional objects, features, and benefits, may be understood through the following illustrative and non-limiting detailed description, with reference to the appended drawings. In the drawings like reference numerals will be used for like elements unless stated otherwise.

All the figures are schematic, not necessarily to scale, and generally only show parts which are necessary to elucidate example embodiments; other parts may be omitted or merely suggested.

DETAILED DESCRIPTION

Figure 1A:
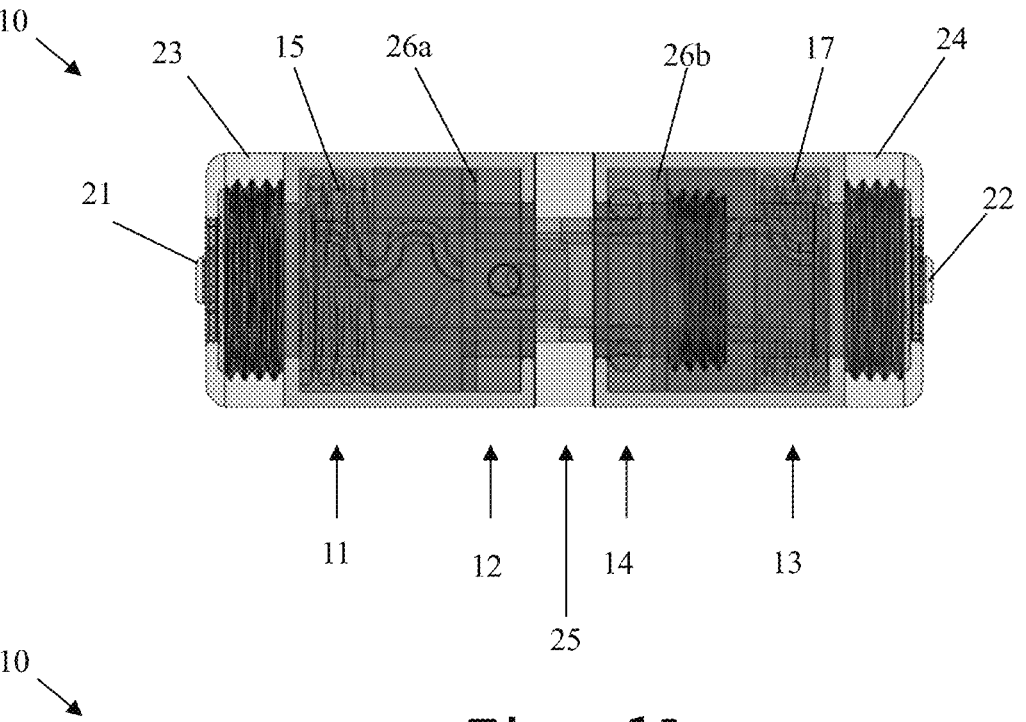
FIG. 1A shows an ingestible device in an inactivated state, according to an example embodiment.

With respect to FIG. 1A, an exemplary embodiment of an ingestible device 10 for simultaneously sampling material and releasing a substance at least one time is illustrated. In this context, it is noted that the ingestible device 10 is in an inactivated state.

According to FIG. 1A, the ingestible device 10 comprises a first chamber 11 being enlargeable in space, comprising an inlet, and to be filled with the material to be sampled, a second chamber 12 being diminishable in space, comprising an outlet, and containing the substance to be released, and a reversible actuating mechanism. In this context, the reversible actuating mechanism is configured such that triggering the reversible actuating mechanism leads to an enlargement of the first chamber 11 and to a simultaneous diminishment of the second chamber 12. It is noted that the first chamber 11 takes in the material through the inlet due to an under pressure, and the second chamber 12 releases the substance through the outlet due to an over pressure.

The outlet can include an outlet valve configured to prevent release of any substance before triggering.

As it can also be seen from FIG. 1A, the ingestible device 10 further comprises a third chamber 13 being enlargeable in space, comprising a further inlet, and to be filled with further material to be sampled, a fourth chamber 14 being diminishable in space, comprising a further outlet, and containing a further substance to be released, and a further reversible actuating mechanism. In this context, the further reversible actuating mechanism is configured such that triggering the further reversible actuating mechanism leads to an enlargement of the third chamber 13, the third chamber 13 thereby taking in further material through the further inlet due to an under pressure, and to a simultaneous diminishment of the fourth chamber 14, the fourth chamber 14 thereby releasing the further substance through the further outlet due to an over pressure.

The further outlet can include a further outlet valve configured to prevent release of any further substance before triggering.

Figure 2A:
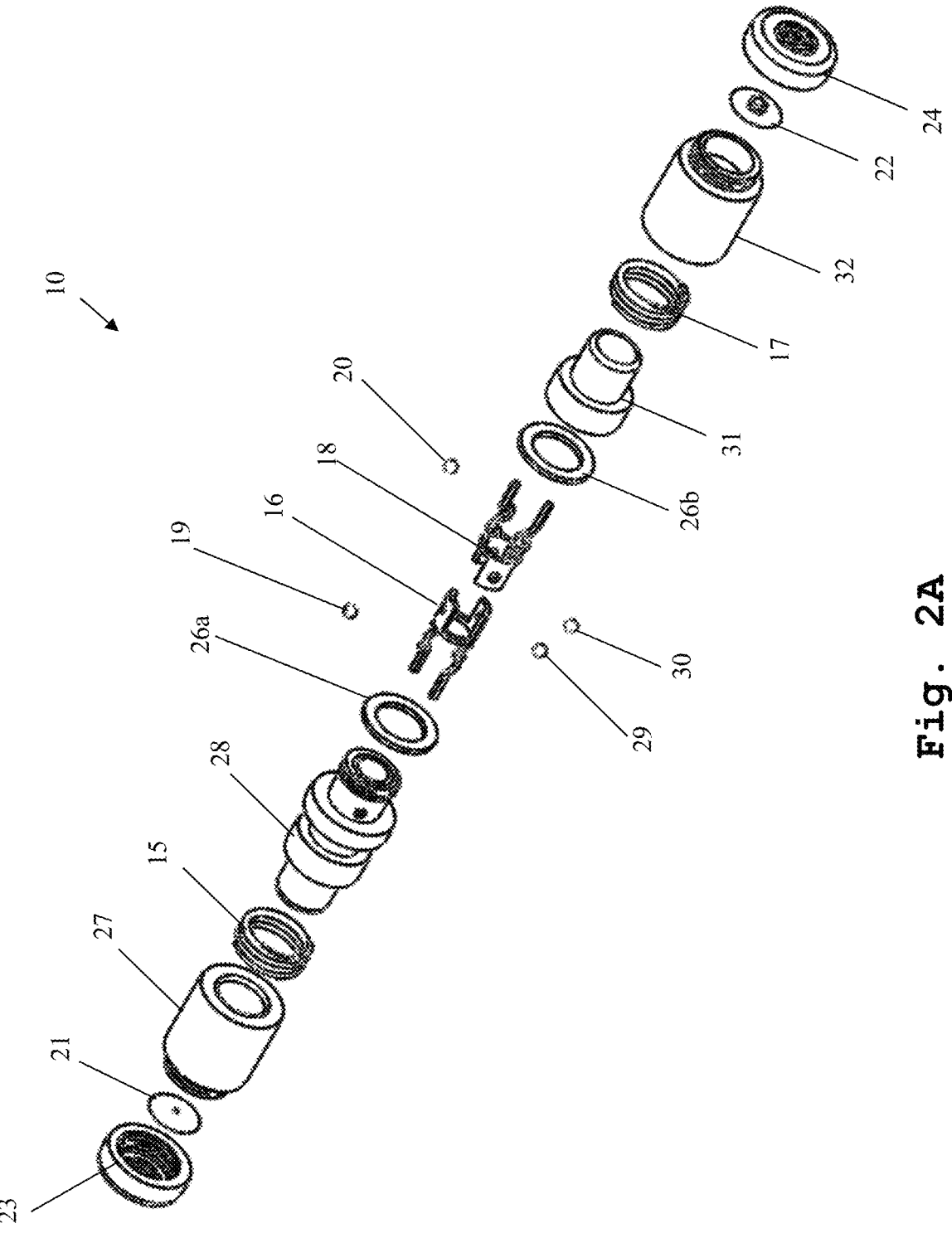
FIG. 2A shows the device of FIG. 1A or FIG. 1B in an expanded view, according to an example embodiment.

With respect to the above-mentioned reversible actuating mechanism, it is noted that the reversible actuating mechanism comprises a spring 15 being compressed if the reversible actuating mechanism has not been triggered yet, an electrically conductive alloy portion 16, which can be seen from the corresponding exploded view of FIG. 2A, being conductively connected to an energy source if the reversible actuating mechanism is triggered. In this context, the electrically conductive alloy portion 16 is configured such that connecting the electrically conductive alloy portion 16 to the energy source leads to a reversible deformation of the electrically conductive alloy portion 16 due to Joule heating.

In addition to this, the spring 15 is arranged with respect to the electrically conductive alloy portion 16 such that the reversible deformation of the electrically conductive alloy portion 16 leads to a decompression of the spring 15, wherein the spring 15 is arranged with respect to the first chamber 11 such that the first chamber 11 is enlarged in the case of the decompression of the spring 15, and wherein the spring 15 is arranged with respect to the second chamber 12 such that the second chamber 12 is diminished in the case of the decompression of the spring 15.

In accordance with the exploded view of FIG. 2A, the reversible actuating mechanism further comprises at least one ball release member, exemplarily two ball release members 19 and 29. In this context, the ball release members 19 and 29 are configured such that the reversible deformation of the electrically conductive alloy portion 16 leads to a movement of the two ball release members 19, 29 into two corresponding indentations, thereby decompressing the spring 15.

Moreover, also with respect to FIG. 2A, it is noted that the above-mentioned further reversible actuating mechanism further comprises at least one further ball release member, exemplarily two ball release members 20 and 30. In this context, the further ball release members 20 and 30 are configured such that the further reversible deformation of the further electrically conductive alloy portion 18 leads to a movement of the two further ball release members 20, 30 into two corresponding further indentations, thereby decompressing the further spring 17.

In accordance with FIG. 2A, with respect to the further reversible actuating mechanism, it is noted that the further reversible actuating mechanism comprises a further spring 17 being compressed if the further reversible actuating mechanism has not been triggered yet, a further electrically conductive alloy portion 18 being conductively connected to a further energy source if the further reversible actuating mechanism is triggered. In this context, the further electrically conductive alloy portion 18 is configured such that connecting the further electrically conductive alloy portion 18 to the further energy source leads to a reversible deformation of the further electrically conductive alloy portion 18 due to Joule heating.

In addition to this, the further spring 17 is arranged with respect to the further electrically conductive alloy portion 18 such that the reversible deformation of the further electrically conductive alloy portion 18 leads to a decompression of the further spring 17, wherein the further spring 17 is arranged with respect to the third chamber 13 such that the third chamber 13 is enlarged in the case of the decompression of the further spring 17, and wherein the further spring 17 is arranged with respect to the fourth chamber 14 such that the fourth chamber 14 is diminished in the case of the decompression of the further spring 17.

With respect to the above-mentioned inlet, it is noted that the inlet comprises a valve, for example a passive valve, which may be a passive one-way valve, e.g., an umbrella valve such as the umbrella valve 21 of FIG. 2A. With respect to the above-mentioned further inlet, it is noted that the further inlet comprises a further valve, for example a further passive valve, which may be a further passive one-way valve, e.g., a further umbrella valve such as the further umbrella valve 22 of FIG. 2A.

Furthermore, as it can be seen from FIG. 1A or FIG. 2A, respectively, the first chamber 11 comprises a removable portion, exemplarily a screwable cap 23, for access to the internal space of the first chamber 11. Moreover, the third chamber 13 comprises a further removable portion, exemplarily a further screwable cap 24, for access to the internal space of the third chamber 13.

In accordance with FIG. 1A, the ingestible device 10 further comprises a body portion 25 providing a hollow inner space being, e.g., sealed against the environment of the body portion 25 exemplarily with the aid of two O-rings 26a and 26b. In this context, the first chamber 11 and the second chamber 12 are attached to the body portion 25, and the third chamber 13 and the fourth chamber 14 are attached to the body portion 25 exemplarily in a symmetric manner to the first chamber 11 and the second chamber 12.

The body portion 25, for example the hollow inner space of the body portion 25, comprises at least one of an energy source for supplying the reversible actuating mechanism and the further reversible actuating mechanism, a remote trigger unit, being supplied by the energy source, for receiving at least one remote trigger signal in order to trigger the reversible actuating mechanism and the further reversible actuating mechanism, a data recording unit for recording data, e.g., environment data and/or localization data, during usage of the ingestible device 10.

In addition to this or as an alternative, the body portion 25, e.g., a portion other than the hollow inner space of the body portion 25, may comprise at least one sensor, e.g., a pH-value sensor. It is further noted that the ingestible device 10 has the shape of a pill or a cylinder.

Figure 1B:
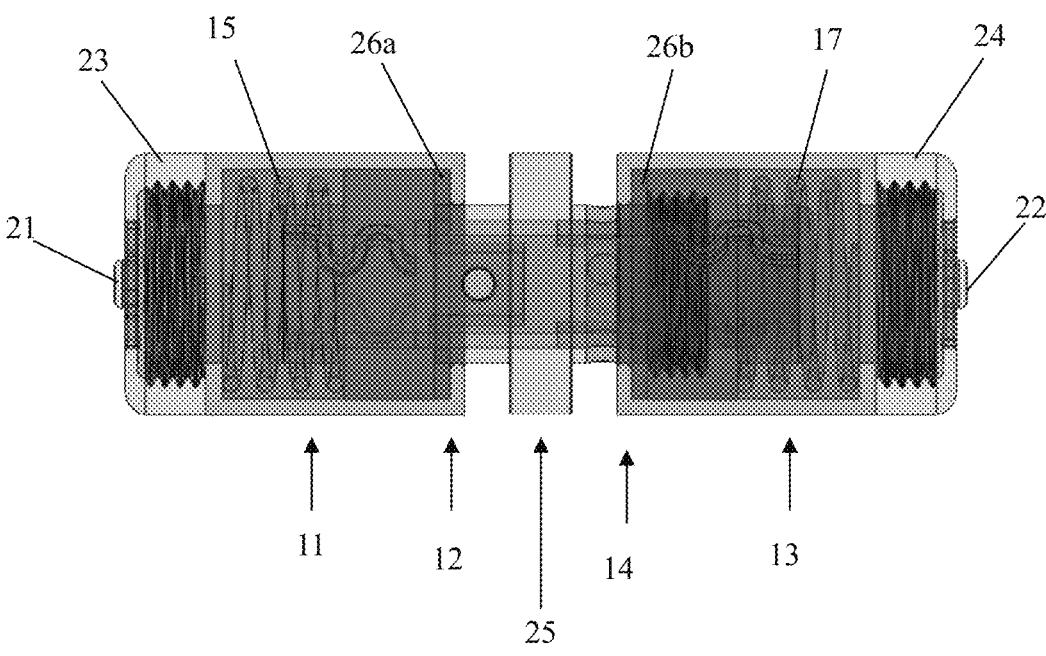
FIG. 1B shows the device of FIG. 1A in an activated state, according to an example embodiment.

As it can be seen from FIG. 1A showing the inactivated state of the ingestible device and FIG. 1B illustrating the activated state of the same, the diameter of the ingestible device 10 does not change after activation, whereas the length of the same increases due to activation. In this context, the length of the ingestible device 10 is lower than 24 millimeters exemplarily after the reversible actuating mechanism has been triggered and/or the further reversible actuating mechanism has been triggered, whereas the diameter of the ingestible device 10 is lower than 10 millimeters.

With respect to the inactivated state of the ingestible device 10 according to FIG. 1A, it is noted that in this state, neither the reversible actuation mechanism nor the further reversible actuation mechanism have been triggered yet. Accordingly, both the spring 15 and the further spring 17 are still compressed. With respect to the activated state of the ingestible device according to FIG. 1B, it is further noted that in this state, at least one, exemplarily both, of the reversible actuation mechanism and the further reversible actuation mechanism has been triggered, which leads to a decompression of the respective one of the springs 15 and the further spring 17.

Again, with respect to FIG. 2A, it is noted that the screwable cap 23, the umbrella valve 21, the spring 15, the O-ring 26a, the further O-ring 26b, the further spring 17, the further umbrella valve 22, the further screwable cap 24, and the body portion 25 have already been explained in the context of FIG. 1A or FIG. 1B, respectively. Furthermore, in view of FIG. 2A, the electrically conductive alloy portion 16, the further electrically conductive alloy portion 18, the ball release members 19 and 29, and the further ball release members 20 and 30 have already been discussed above. Accordingly, the remaining parts depicted in FIG. 2A are explained in the following.

According to FIG. 2A, the above-mentioned body portion 25 of FIG. 1A or FIG. 1B, respectively, comprises a first body part 28 and a second body part 31. Furthermore, a first outer shell 27 of the ingestible device 10 comprises the first body part 28. Additionally, the ingestible device 10 comprises a second outer shell 32 comprising the second body part 31.

Figure 3:
FIG. 3 shows an electronics module comprising a reversible actuating mechanism, depicted in a top-side view, according to an example embodiment.
Figure 3:
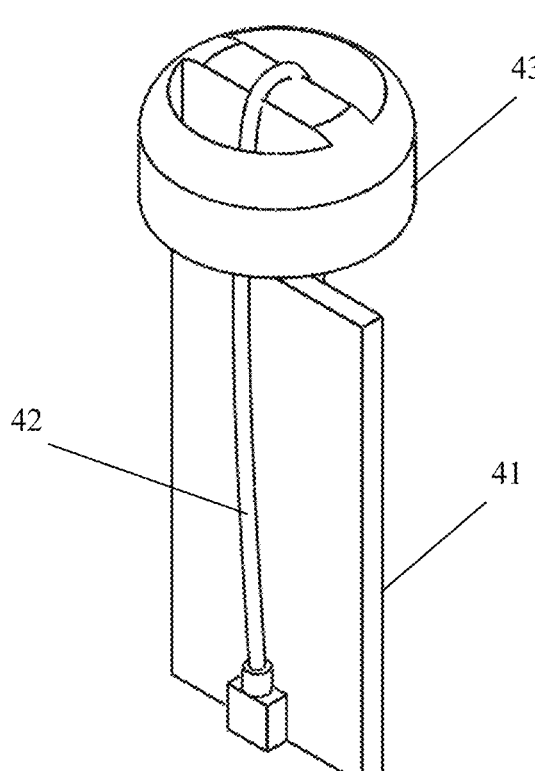

With respect to the body portion 25, it is noted that the body portion, e.g., its hollow inner space, may comprise an electronics module such as the electronics module 40 according to FIG. 3. The electronics module can include at least one of an energy source for supplying the reversible actuating mechanism and the further reversible actuating mechanism, a remote trigger unit, being supplied by the energy source, for receiving at least one remote trigger signal in order to trigger the reversible actuating mechanism and the further reversible actuating mechanism, a data recording unit for recording data, e.g., environment data and/or localization data, during usage of the ingestible device 10.

Figure 2B:
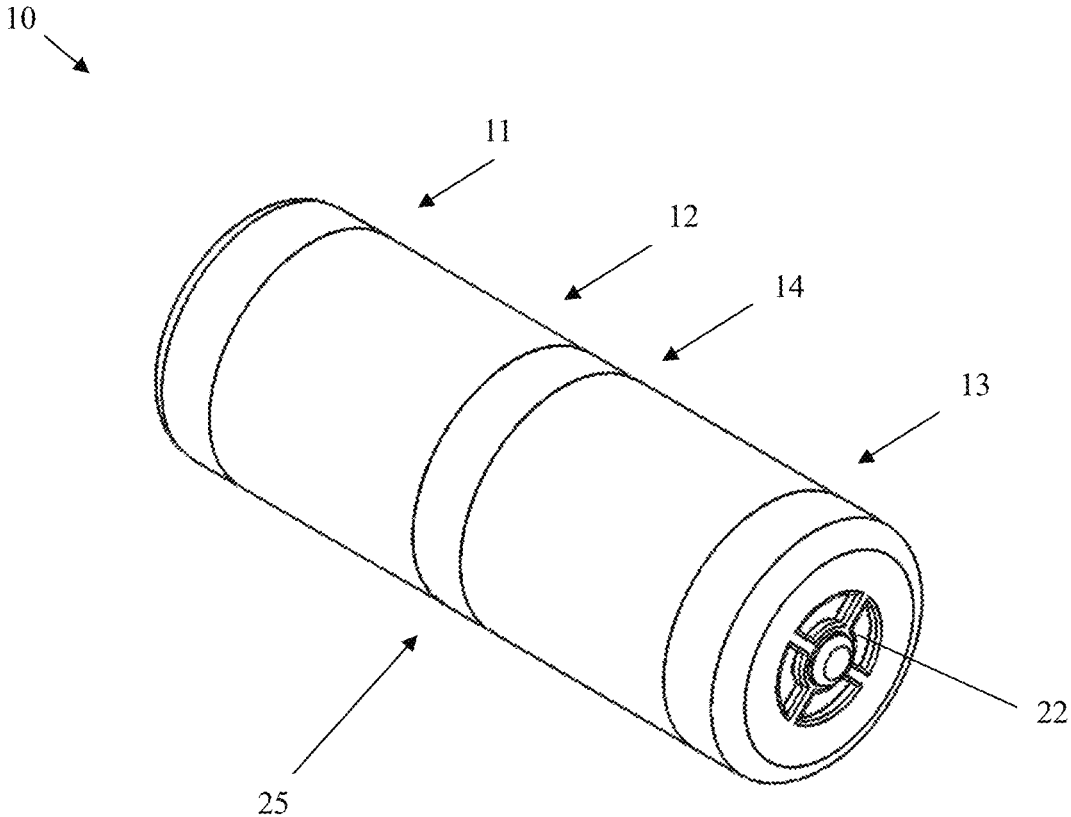
FIG. 2B shows the elements of FIG. 2A in a fully assembled and inactivated state, according to an example embodiment.

Now, before the above-mentioned FIG. 3 is explained in the following, it is noted that FIG. 2B depicts the illustration of FIG. 2A in a fully assembled manner and in an inactivated state. FIG. 3 shows an exemplary embodiment of an electronics module 40 comprising a reversible actuating mechanism in a top-side view. The electronics module 40 exemplarily comprises a printed circuit board 41, a shape-memory alloy wire 42, and an actuator ring 43.

Accordingly, in this exemplary embodiment of FIG. 3, at least one, potentially both, of the above-mentioned electrically conductive alloy portion 16 and the further electrically conductive alloy portion 18 is embodied as the shape-memory alloy wire 42. Furthermore, also in this exemplary embodiment according to FIG. 3, at least one, potentially both, of the reversible actuating mechanism and the further reversible actuating mechanism is embodied as the actuator ring 43.

The actuator ring 43 can be configured to move out of the way such that the ball release member can move into the indentation releasing the spring.

The exemplary embodiment of the ingestible device 10 described above can be seen as a remotely activatable dual-sampling pill, which includes only a few elements. Thus, manufacturing such an ingestible device can be accomplished for low cost.

The cap section, such as the first and second body parts 28, 31 or the first and second outer shells 27, 32, respectively, of FIG. 2A, slides over the electronics module such as the electronics module 40 of FIG. 3. The cap lid, such as the screwable cap 23 and the further screwable cap 24 of FIG. 2A, can be screwed on the cap section. Furthermore, the cap lid contains a passive umbrella valve such as the umbrella valve 21 and the further umbrella valve 22 according to FIG. 2A. This passive umbrella valve enables one-directional flow, enabling sampling and closing of the top of the sample chamber such as the first chamber 11 and the third chamber 13 of FIG. 1A. The bottom of the sample chamber is sealed off by an O-ring, such as the O-rings 26a, 26b according to FIG. 1A or FIG. 2A, respectively, that is placed just below the top ridge of the electronics module.

The screwable cap lid provides easy access to the sample chamber. This can reduce the effort needed to inject a quencher as well as to effect sample removal. The overall size of the remotely activatable dual-sampling pill in the inactivated state can be less that 24 millimeters in length and/or 9 millimeters in diameter to make the pill relatively easy to swallow. The hollow electronics module or the hollow body portion can have enough space inside to implement the power source, the sensors, and further electronics such as communication, e.g., wireless communication, and at least one antenna.

The middle section of the body portion, such as the body portion 25 of FIG. 1A, can be directly exposed to the gastrointestinal (GI) fluid. Accordingly, sensors implemented in this area of the pill can measure GI fluid in real time. These measurements can facilitate determining the location of the pill and give insight in patient health or animal health.

The power source or energy source can generate sufficient current to activate the reversible actuating mechanism. The reversible actuating mechanism can cause a downward motion of the sleeve such as the electrically conductive alloy portion 16 and the further electrically conductive alloy portion 18 of FIG. 2A. Due to this motion, pockets, such as the indentation and the further indentation, open into which the respective ball release members, such as the ball release members 19, 20, 29, 30 of FIG. 2A, can medially withdraw, relieving them from the cap section retaining function, allowing a vertical movement of the cap section generated by the compression spring such as the spring 15 and the further spring 17.

The compression spring is located in between the cap section and the top ridge of the electronics module. This lateral movement enlarges the volume of the sample chamber, creating an under pressure that will be released by taking in GI fluid from the GI tract at the desired location. Simultaneously, the lateral movement also leads to a volume reduction in the drug container, such as the second chamber 12 and the fourth chamber 14 of FIG. 2A, medial to the spring, enabling drug release at the desired location.

As it can generally be seen, the remotely activatable dual-sampling pill includes three major parts that slide over each other, allowing for an expansion of the device.

Once, the device reaches the activated state, it hovers around dimensions not exceeding 24 millimeters in length and/or 9 millimeters in diameter. As already mentioned above, the remotely activatable dual-sampling pill comprises only few elements and most or even all of them are very easy to fabricate, for example via 3D printing among other methods. The sliding mechanism is a reliable way to achieve sampling, while diminishing the chance of failure. Moreover, the remotely activatable dual-sampling pill in its entirety may be nonmagnetic, making it MM (magnetic resonance imaging) compatible.

The ingestible device can include two reversible actuating mechanisms, one for each sampling chamber. These mechanisms may comprise a bend shape-memory metal alloy wire that after heating assumes its austinite phase resulting in a decrease in wire length. The increase in wire temperature is caused by Joule heating induced by a current from the energy source. The energy source can deliver sufficient current through the wire via two electrodes connected on both ends of the wire closing the circuit. As the wire length is reduced it pulls the sleeve down, allowing two ball release members to move inward, enabling the capsule module to freely move in a lateral direction. The lateral movement is achieved by a compression spring.

This reversible actuating mechanism can be configured to operate using relatively little current as well as a relatively low voltage, and thus may avoid the use of large batteries making it suitable for use in a remotely activatable dual-sampling pill. Sampling and delivery are facilitated by the previously discussed lateral movement of the capsule as caused by the release of the compression spring. The lateral movement of the capsule induces an expansion of the sample chamber forming an under pressure inside the sample chamber that can be released by taking in a sample. Synchronously, the lateral movement of the capsule also causes a volume reduction in the drug container medial to the spring, creating an over pressure that can be discharged by drug release.

The ingestible device described herein provides closed off compartments because the sample chambers and drug containers are sealed off by an umbrella valve on one end and by an O-ring on the other end. Both components can be obtained easily and for low cost. An ingestible device as described herein allows for a simplified sample retrieval because the capsule modules have a screwable cap that allows for direct sample removal. Accordingly, the chance of sample spillage is reduced.

The ingestible device described herein provides additional space for sensors because the electronics module of the remotely activatable dual-sampling pill is large enough to contain sensors. The sensors can determine time and position to enable sampling at the correct location in the GI tract. This also may facilitate continuous measurements of GI fluid.

A remotely activatable dual-sampling pill or other ingestible device as described herein may exhibit one or more features:
1. noninvasive active gastrointestinal fluid sampling.
2. simple fabrication, e.g., via 3D printing. Components are easily obtainable.
3. screwable cap lids facilitate simplified, low-effort sample retrieval.
4. the spacious interior of the electronics module provides ample room for the energy source, electronics, and sensors. Such sensors may be configured to measure GI fluid in real time and thus contribute to the location determination of the pill, and give insight into patient health.
5. reduced overall pill size, in the inactivated state makes the administration of the pill more comfortable for the user.
6. MM compatible.
7. built-in localization component.
8. reduced or eliminated sample contamination due to closed off sample chambers by passive umbrella valves and O-rings.
9. easy to assemble.
10. reduced pill size, in the activated state, reduced the chance of pill retention.
11. delivery of a fluid sample into the GI tract (for instance, drug delivery). The same actuation mechanism is used for sampling and simultaneous delivery.

Figure 4:
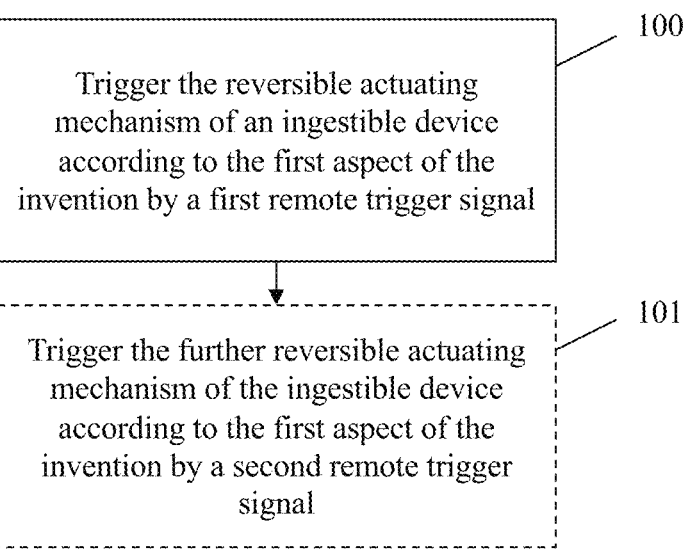
FIG. 4 shows a flow chart of an example method.

FIG. 4 shows a flow chart of an embodiment of a method for using an ingestible device as described herein (e.g., the ingestible device 10). In step 100, the reversible actuating mechanism of the ingestible device is triggered by a first remote trigger signal. In addition to this or as an alternative, in step 101, the further reversible actuating mechanism of the ingestible device is triggered by transmitting a second remote trigger signal.

While various embodiments have been described above, it should be understood that they have been presented by way of example only, and not limitation. Numerous changes to the disclosed embodiments can be made in accordance with the disclosure herein without departing from the scope of the present disclosure. Thus, the breadth and scope of the present disclosure should not be limited by any of the above described embodiments.

Although the present disclosure has been illustrated and described with respect to one or more implementations, equivalent alterations and modifications will occur to others skilled in the art upon the reading and understanding of this specification and the drawings. In addition, while a particular feature may have been disclosed with respect to only one of several implementations, such feature may be combined with one or more other features of the other implementations as may be desired for a particular application.

In the above the various embodiments herein have mainly been described with reference to a limited number of examples. However, as is readily appreciated by a person skilled in the art, other examples than the ones disclosed above are equally possible within the scope of the present disclosure, for example those defined by the appended claims.

What is claimed is:

1. An ingestible device for sampling material at least one time, the ingestible device comprising:

a first chamber having an enlargeable volume, wherein the first chamber comprises an inlet, and wherein the first chamber is capable of being filled with the material to be sampled;

a second chamber having a diminishable volume, wherein the second chamber comprises an outlet;

a third chamber having an enlargeable volume, wherein the third chamber comprises a further inlet, and wherein the third chamber is capable of being filled with further material to be sampled;

a fourth chamber having a diminishable volume, wherein the fourth chamber comprises a further outlet;

a reversible actuating mechanism, wherein the reversible actuating mechanism is configured to, in response to triggering the reversible actuating mechanism, cause (i) an enlargement of the first chamber, thereby collecting the material to be sampled in the first chamber via the inlet and (ii) a diminishment of the second chamber; and a further reversible actuating mechanism, wherein the further reversible actuating mechanism is configured to, in response to triggering the further reversible actuating mechanism, cause (i) an enlargement of the third chamber, thereby collecting further material in the third chamber via the further inlet and (ii) a diminishment of the fourth chamber.

2. The ingestible device of claim 1, wherein the inlet is configured to be sealed following collection of the material in the first chamber when the material is collected.

3. The ingestible device of claim 1, further comprising: a substance to be released that is disposed within the second chamber, wherein diminishment of the second chamber results in release of the substance to be released via the outlet.

4. The ingestible device of claim 3, wherein the substance to be released is a drug.

5. The ingestible device of claim 1, wherein at least one of: (i) the first chamber and the second chamber are axisymmetric with respect to the third chamber and the fourth chamber; (ii) the first chamber and the second chamber are point-symmetric with respect to the third chamber and the fourth chamber, (iii) the first chamber and the second chamber are rotationally symmetric with respect to the same axis, (iv) the reversible actuating mechanism is at least one of axisymmetric or point-symmetric with respect to the further reversible actuating mechanism, or (v) the reversible actuating mechanism and the further reversible actuating mechanism are rotationally symmetric with respect to the same axis.

6. The ingestible device of claim 1, wherein the reversible actuating mechanism comprises:

a spring that is compressed prior to triggering the reversible actuating mechanism; and an electrically conductive alloy portion, wherein triggering the reversible actuating mechanism comprises conductively connecting the electrically conductive alloy portion to an energy source, wherein connecting the electrically conductive alloy portion to the energy source results in a reversible deformation of the electrically conductive alloy portion due to Joule heating, wherein such a reversible deformation of the electrically conductive alloy portion results in a decompression of the spring, wherein such a decompression of the spring results in (i) enlargement of the first chamber and (ii) diminishment of the second chamber.

7. The ingestible device of claim 6, wherein the reversible actuating mechanism further comprises:

at least one ball release member, wherein the reversible deformation of the electrically conductive alloy portion results in a movement of the at least one ball release member into at least one indentation, thereby decompressing the spring.

8. The ingestible device of claim 1, wherein the inlet comprises a passive one-way valve.

9. The ingestible device of claim 8, wherein the passive one-way valve is an umbrella valve.

10. The ingestible device of claim 1, wherein the first chamber comprises a removable portion that provides access to an internal space of the first chamber.

11. The ingestible device of claim 10, wherein the removable portion is a screwable cap.

12. The ingestible device of claim 1, wherein the material to be sampled is gastrointestinal content.

13. The ingestible device of claim 1, further comprising a stabilizing substance disposed in the first chamber.

14. The ingestible device of claim 13, wherein the stabilizing substance comprises a quencher that reduces a rate of chemical reaction of the material to be sampled.

15. The ingestible device of claim 1, wherein the ingestible device further comprises a body portion having a hollow inner space that is sealed against an environment of the body portion, wherein the first chamber and the second chamber are attached to the body portion.

16. The ingestible device of claim 15, further comprising, disposed within the hollow inner space of the body portion, at least one of:

an energy source configured to supply energy to the reversible actuating mechanism;

a remote trigger unit to receive at least one remote trigger signal and, in response to receiving the at least one remote trigger signal, trigger the reversible actuating mechanism;

a data recording unit configured to record at least one of environment data or localization data;

a wireless data transmission unit configured to wirelessly transmit at least one of environment data or localization data; or a pH-value sensor.

17. The ingestible device of claim 1, wherein a length of the ingestible device is less than 24 millimeters and a diameter of the ingestible device is less than 9 millimeters.

18. The ingestible device of claim 1, wherein the ingestible device has a shape of a pill or cylinder.

19. The ingestible device of claim 1, further comprising a stabilizing substance disposed in the third chamber.

* * * * *